(12) United States Patent
Dick et al.

(10) Patent No.: US 11,311,418 B2
(45) Date of Patent: Apr. 26, 2022

(54) APPARATUS FOR INDIVIDUAL THERAPY PLANNING AND POSITIONALLY ACCURATE MODIFICATION OF AN OPTICAL ELEMENT

(71) Applicant: Carl Zeiss Meditec AG, Jena (DE)

(72) Inventors: Manfred Dick, Gefell (DE); Matthias Reich, Jena (DE); Diego Zimare, Pausa (DE)

(73) Assignee: CARL ZEISS MEDITEC AG, Jena (DE)

( * ) Notice: Subject to any disclaimer, the term of this patent is extended or adjusted under 35 U.S.C. 154(b) by 349 days.

(21) Appl. No.: 16/513,821

(22) Filed: Jul. 17, 2019

(65) Prior Publication Data

US 2019/0336342 A1    Nov. 7, 2019

Related U.S. Application Data

(63) Continuation of application No. 15/257,934, filed on Sep. 7, 2016, now Pat. No. 10,398,600, which is a
(Continued)

(30) Foreign Application Priority Data

Aug. 7, 2006 (DE) .................. 10 2006 036 800.2

(51) Int. Cl.
*A61F 9/008* (2006.01)
*A61B 3/10* (2006.01)
*A61B 3/103* (2006.01)

(52) U.S. Cl.
CPC .......... *A61F 9/00836* (2013.01); *A61B 3/102* (2013.01); *A61B 3/103* (2013.01);
(Continued)

(58) Field of Classification Search
CPC .. A61F 9/008; A61F 9/00804; A61F 9/00821; A61F 9/00836; A61F 9/00838;
(Continued)

(56) References Cited

U.S. PATENT DOCUMENTS 5,609,573 A    3/1997  Sandock
5,728,156 A *  3/1998  Gupta .................. A61F 2/1613
                                              623/6.26
(Continued)

FOREIGN PATENT DOCUMENTS

DE    102004009212 A1    9/2005
WO    WO 0119303 A1      3/2001
(Continued)

OTHER PUBLICATIONS

International Search Report for International No. PCT/EP2007/006898 dated Mar. 8, 2008.
(Continued)

*Primary Examiner* — Vi X Nguyen
(74) *Attorney, Agent, or Firm* — Leydig, Voit & Mayer, Ltd.

(57) ABSTRACT

A method for detecting structures within an optical element of an eye and processing the optical element as a function of the detected structures includes acquiring, by a detection device, geometric data of an eye, transferring, by the detection device, the geometric data of the eye to a controller, calculating, by the controller, target coordinates for a processing device including a laser, the processing device being connected to the controller, and applying a beam produced by the laser to the eye according to the target coordinates calculated by the controller so as to process the optical element.

5 Claims, 3 Drawing Sheets

Related U.S. Application Data continuation of application No. 12/376,847, filed as application No. PCT/EP2007/006898 on Aug. 3, 2007, now Pat. No. 9,463,115.

(52) U.S. Cl.
CPC .......... *A61B 3/1005* (2013.01); *A61B 3/1025* (2013.01); *A61F 9/008* (2013.01); *A61F 9/00838* (2013.01); *A61F 2009/0088* (2013.01); *A61F 2009/00851* (2013.01); *A61F 2009/00887* (2013.01); *A61F 2009/00895* (2013.01)

(58) Field of Classification Search
CPC .. A61F 2009/00895; A61F 2009/00851; A61F 2009/0088; A61F 2009/00887; A61F 2009/00872
See application file for complete search history.

(56) References Cited

U.S. PATENT DOCUMENTS

| | | | |
|---|---|---|---|
| 5,920,373 A | 7/1999 | Bille | |
| 6,099,522 A | 8/2000 | Knopp et al. | |
| 6,577,394 B1 | 6/2003 | Zavislan | |
| 6,755,819 B1 | 6/2004 | Waelti | |
| 7,211,078 B2 | 5/2007 | Feige et al. | |
| 8,221,400 B2 | 7/2012 | Lubatschowski et al. | |
| 2002/0180931 A1* | 12/2002 | Dick | A61B 3/14 351/211 |
| 2003/0220629 A1 | 11/2003 | Billie et al. | |
| 2004/0199149 A1 | 10/2004 | Myers et al. | |
| 2005/0165387 A1 | 7/2005 | Lubatschowski et al. | |
| 2007/0179478 A1 | 8/2007 | Dobschal et al. | |
| 2011/0205488 A1 | 8/2011 | Vogelsang et al. | |

FOREIGN PATENT DOCUMENTS

| | | |
|---|---|---|
| WO | WO 03039356 A2 | 5/2003 |
| WO | WO 2005070358 A1 | 8/2005 |
| WO | WO 2006074469 A | 7/2006 |

OTHER PUBLICATIONS

H.B. Dick et al. „Dynamische Aberrometrie waehrend der Akkomodation phaker Augen sowie Augen mit potenziell akkommodativer Ontraokularlinse [Dynamic aberrometry during accomodation of phakic eyes and eyes with potentially accomodative intraocular lenses], Der Ophthalmologe: Zeitschrift der deutschen Ophthalmologischen Gesellschaft No. 2002, vol. 99, No. 11, Nov. 2002, pp. 825-834, XP002470325.

\* cited by examiner

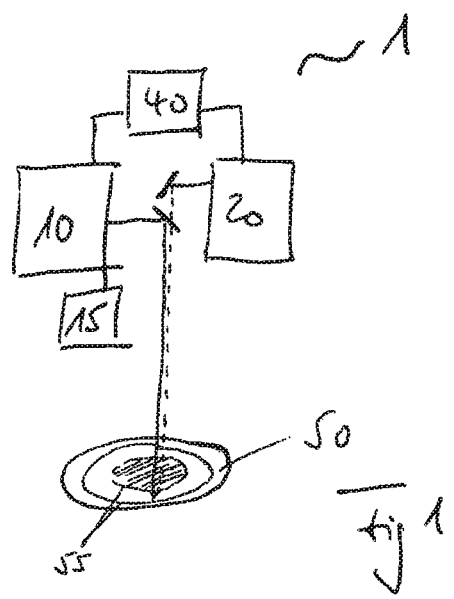

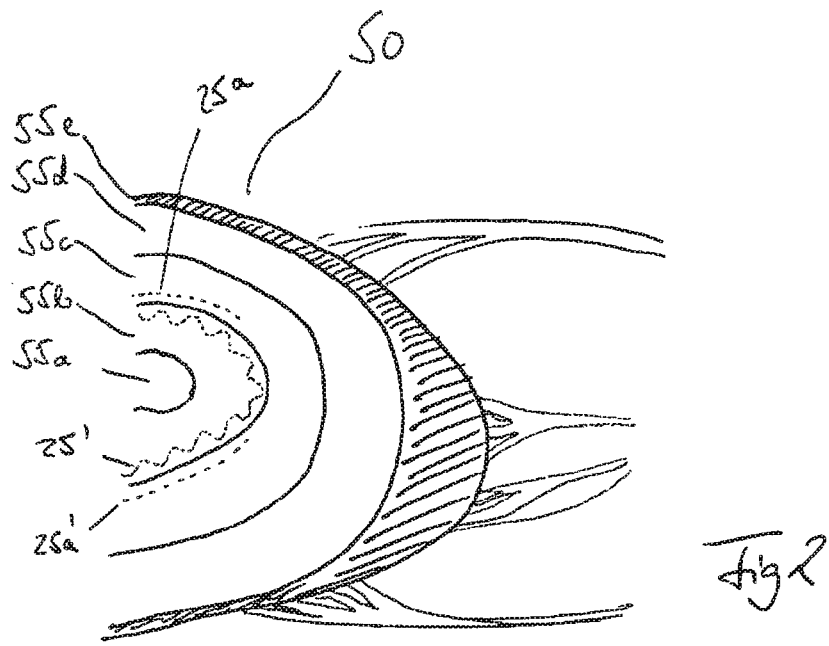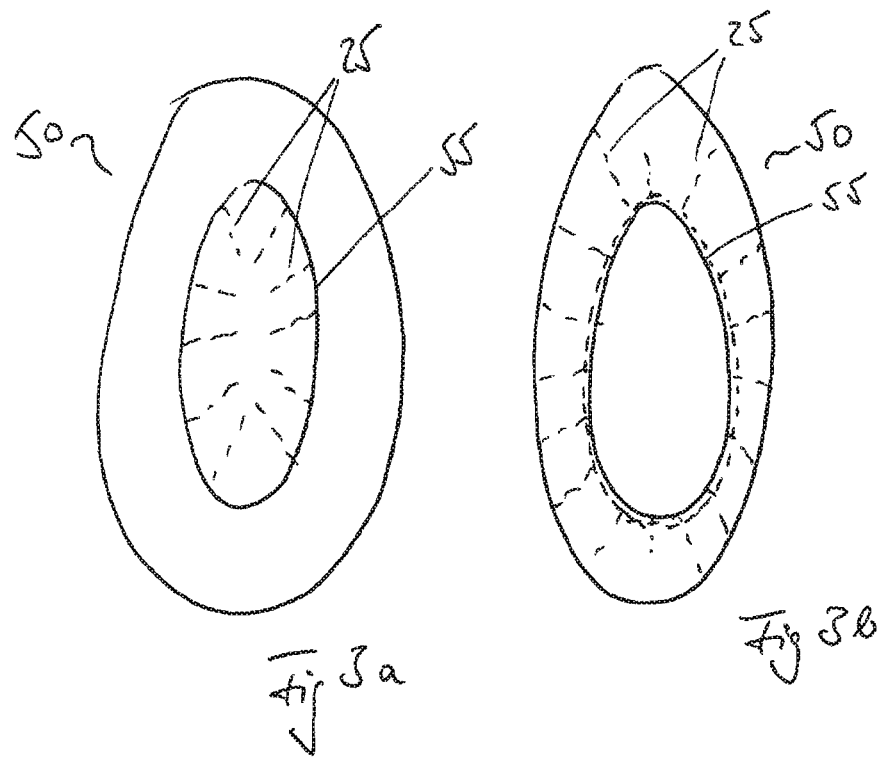

APPARATUS FOR INDIVIDUAL THERAPY PLANNING AND POSITIONALLY ACCURATE MODIFICATION OF AN OPTICAL ELEMENT

CROSS REFERENCE TO RELATED APPLICATIONS

This application is a continuation of U.S. patent application Ser. No. 15/257,934, which is a continuation of U.S. Pat. No. 9,463,115, filed on Feb. 9, 2009, which is a U.S. National Phase application under 35 U.S.C. § 371 of International Application No. PCT/EP2007/006898, filed on Aug. 3, 2007, which claims priority to German Patent Application No. DE 10 2006 036 800.2, filed on Aug. 7, 2006.

FIELD

The present invention relates to an apparatus for individual therapy planning and positionally accurate modification of an optical element. Specifically, the present invention relates to a navigation apparatus for optically analyzing and modifying an optical element and, more particularly, to a navigation apparatus for optically analyzing and modifying an aged human eye to treat presbyopia.

BACKGROUND

In ophthalmology, it is known to shape the cornea by surgery on tissue to thereby correct myopia, hyperopia and astigmatisms. This is done using laser beams, for example, of an ArF excimer laser, whose radiation pulses have a wavelength of 193 nm. In addition to laser-surgical, refractive correction of the cornea, methods have been described for the therapy of the eye lens to treat presbyopia. These methods attempt, by way of suitable cuts or bubble fields, to return the hardened lens to a condition in which it can be better deformed by the capsular bag or ciliary muscle. This is basically intended to partially restore the accommodative ability of the lens.

Document WO2005/070358 describes simple cutting geometries, which are intended to increase the flexibility in homogeneous materials. The disclosed methods and cutting geometries do not take into account the individual geometry or the inner structure of the eye lens.

SUMMARY

In an embodiment, the present invention provides a method for detecting structures within an optical element of an eye and processing the optical element as a function of the detected structures. The method includes acquiring, by a detection device, geometric data of an eye, transferring, by the detection device, the geometric data of the eye to a controller, calculating, by the controller, target coordinates for a processing device including a laser, the processing device being connected to the controller, and applying a beam produced by the laser to the eye according to the target coordinates calculated by the controller so as to process the optical element.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIG. 1 is a schematic view of a navigation apparatus according to an embodiment of the present invention;

FIG. 2 is a schematic view of the construction of the human eye lens;

FIGS. 3a and 3b are schematic views illustrating two cutting patterns in the optical element.

DETAILED DESCRIPTION

Figure 4:
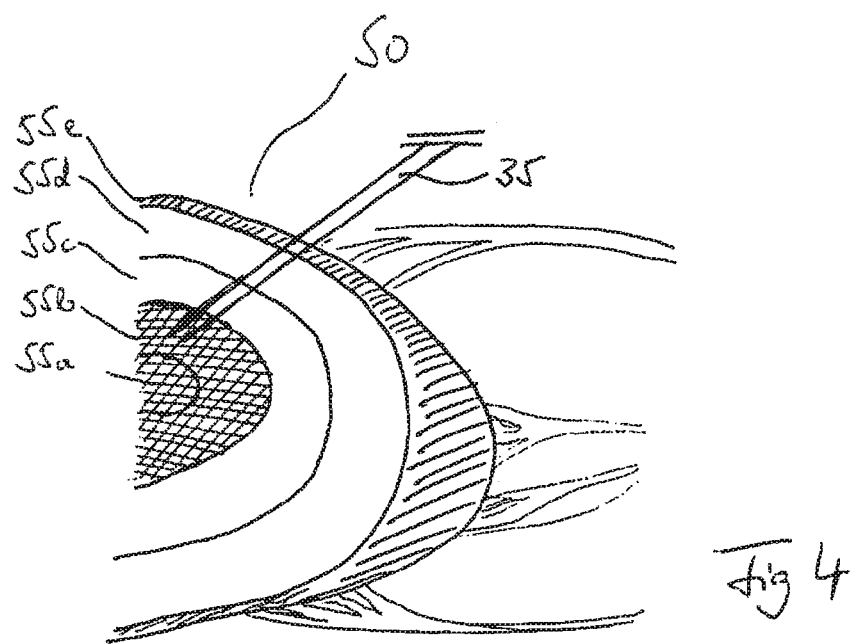
FIG. 4 is a schematic view of a further embodiment of the present invention, which is used in partial phacoemulsification.

An embodiment of the present invention is to provide an inventive navigation apparatus for optically analyzing the inner structure and/or the individual position of an optical element and for modifying and/or processing the optical element, said navigation apparatus including a detection device having an aperture smaller than 0.25, and further including a processing device adapted to be guided along, or in a fixed relationship to, the analyzed inner structure of the optical element.

An embodiment of the present invention provides an ophthalmo-surgical device system, and instructions for using it, for preparing and removing transparent biological tissue in a very gentle and accurate manner, especially in the eye, and more particularly in the human eye lens, during refractive laser surgery or cataract surgery, especially to treat presbyopia by restoring the accommodative ability of the lens body.

A navigation apparatus includes a plurality of components and makes it possible, on the one hand, to explore and analyze the structure within an optical element and, on the other hand, to process and/or modify this optical element at the then defined locations. Such a navigation apparatus allows structures within the optical element, and the processing of the optical element with point accuracy as a function of the detected structures. Particularly preferably, the apparatus can be used for ophthalmological purposes.

An optical element is an element allowing an optical path to pass therethrough. Preferably, the element has a different refractive index than that of the surrounding medium. Particularly preferably, the refractive index of the optical element is greater than that of the surrounding medium. The optical element is the area or object which is examined and/or processed using the navigation apparatus. The optical element preferably has inner structures. For example, the optical element may have a multilayer construction, including layers of different refractive index. It is also conceivable for the optical element to have a single-layer construction. Furthermore, the optical element may have an internal pattern of materials having different refractive indices. The optical element may have an optically active shape, such as a lens shape.

The optical analysis is an examination of the optical element using an optical apparatus, preferably an ophthalmological apparatus, which can be used to detect inner structures of the optical element and/or the individual position of the optical element and/or of the respective structures. The inner structures of an optical element may be, for example, interfaces or layers of various elements that make up the optical element. A vitreous body, for example, may be comprised of a core that is surrounded by various additional layers in an onion-like manner. Due to the growth process, the human eye is also composed of various layers, which form an inner structure allowing them to be distinguished from each other. An eye includes an embryonic nucleus, which is surrounded by a fetal nucleus, which in turn is surrounded by an adult nucleus, which in turn is surrounded by a cortex. The respective interfaces between the various nuclei can then be detected as inner structures during optical analysis.

The navigation apparatus is also designed to modify and/or process the optical element, thereby making it possible to change its optical properties.

Thus, it is possible, for example, to alter structures within the optical element, to make incisions, to partially destroy the optical elements and dissolve portions thereof, to change the refractive index of the material of the optical element in specific areas, to form specific cutting geometries in the optical element, and to thereby change the shape and/or flexibility of the optical element, particularly to increase it.

Especially preferably, a provision is made for a detection device to perform the optical analysis of the inner structure of the optical element. This optical detection device is designed to detect, and preferably visualize, inner structures within an optical element. In this connection, the determination of optically refractive properties can be performed using, for example, aberrometers or refractometers, preferably dynamic aberrometers, and expressed in the form of the respective Zernike polynomials. Particularly preferably, it is possible to use dynamic wavefront diagnosis or a system for dynamic stimulation of the aberrometry. The geometric data of an optical element can also be acquired by devices which operate based on optical coherence tomography (OCT), or which include rotating slit Scheimpflug cameras, confocal laser scanners, and ultrasonographs.

In addition to the optical analysis of the inner structure, it is particularly preferred to perform an optical analysis to determine the current age-related condition of the optical element or lens. Thus, in a subsequent step, a therapeutic pattern which is adapted to the individual lens can be applied using, for example, scanned fs laser radiation. This has the advantage over standard forms of treatment that the greatest possible range of accommodation can be provided in an optical element, for example, an aged human eye, with a minimum amount of cut area and therapeutic effort, which avoids excessive therapeutic measures. To this end, for example, dynamic wavefront diagnosis is performed using a dynamic aberrometer or refractometer to determine the dynamic optical properties of the individual eye expressed in the form of the respective Zernike polynomials. In the simplest case, wavefronts are preferably measured for positive accommodation and for negative accommodation and used to determine the associated range of accommodation. Other properties which may be determined include the speed at which the range of accommodation is traversed and/or the wavefront data generated during this process. It is particularly preferred to also determine visual defects of the patients, the topography of the cornea, the respective pupil size, and the illumination parameters of the stimulation target. In this manner, information is obtained about the range of accommodation and the reaction times of the eye. This allows a comprehensive, objective assessment of the dynamic refractive properties of the eye, which can be used, for example, to characterize the degree of presbyopia. This information, too, can be used subsequently, for example, in a controller to calculate an individual cutting pattern and applied by a processing device. In this manner, the accommodation process can also be taken into account in the finite element simulation. The radial offset at the ciliary body of the individual eyes and/or lens images in the accommodated and disaccommodated conditions can then be used to individually determine cuts which will improve the accommodative ability of this particular lens. If the fs-laser cuts are then also integrated in this modeling, the resulting deformations will correlate with the reduced tissue stiffness. In this manner, the range of accommodation can be restored to the greatest extent possible in the individual optomechanical eye model with as few cuts as possible, in particular outside the natural aperture of the pupil during daytime.

Particularly preferably, the aperture, in particular the numerical aperture, of the detection device is smaller than 0.25. Using such an aperture, it is possible to examine and process the lens within an aged human eye.

With such an aperture, a laser focus having a diameter of about 5 μm can be produced within the scanned lens of the human eye while the pupil is wide open, so as to navigate through and treat the lens in a scanning manner. When using a confocal system, the diameter of the confocal aperture in the detector unit can be selected accordingly.

The processing device is a component that allows the optical element to be modified and/or processed. This is preferably done in the interior of the optical element, especially preferably using radiation. The processing device can then be used to change the structure within the optical element. This device allows cuts bubbles, bubble fields, subdisruptive or disruptive regions to be created within the optical element. Particularly preferably, a laser is used as the processing device depending on the material to be processed, the laser being configured to enter the optical element via the optical path, and to produce its effect at a predetermined location therein. In the case of the human eye, it is especially preferred to use a laser system generating pulses having a duration in the femtosecond range (<1 ps) and a wavelength in the visible or NIR range. In this manner, an effect can be achieved within the eye by focusing at the desired depth and because large portions of the eye do not absorb the radiation. It is particularly preferred for the processing device to also include scanners for three-dimensional deflection and alignment of a focused beam.

Preferably, the processing device is moved along, or in a fixed relationship to, the analyzed inner structure of the optical element. Thus, the processing device can be used to produce an effect along the inner structure, for example along the onion-skin-like interface between the individual layers. In this context, "along the structure" means that the effect produced by the processing device in the optical element is spatially oriented relative to the detected inner structures and layers. Thus, the processing device could, for example, produce an effect, such as a cutting pattern, parallel to and at a predetermined distance from the detected interface. It is also possible to select a fixed relationship between the analyzed inner structure and the region of action of the processing device. The detected interface, according to the optical axis of the optical element based on a function to be defined, provides a cutting geometry whose distance from the detected interface or inner structure may differ, for example, between the center of the optical element and the peripheral area. Similarly, it is possible for the cutting plane to extend in a sinusoidal pattern along the detected interface at a distance therefrom. This allows a relationship to be created between the effect of the modification or processing operations performed by the processing device on the one hand, and the detected inner structures on the other, said relationship taking into account the detected conditions.

Also particularly preferably, a controller is provided by which a calculation of the basic data for the processing device is derived from the data or information that is obtained by the detection device. Such a calculation can be based, for example, on the finite element method, and is thus used to determine suitable data representing coordinates on the basis of which the processing device will then perform modifications or processing operations within the optical element. It is then possible, for example, to predetermine an optimized cutting pattern by which, in a human eye, a pattern is defined between, or in relation to, the individual interfaces which pattern will increase the accommodative ability of the eye or optical element by increasing the flexibility of the optical element in the area of the detected inner structures. This makes it possible to improve the accommodative ability of an aged, presbyopic human eye.

In a preferred exemplary embodiment of the present invention, detection device (10) includes a confocal detector and/or a detector based on optical coherence tomography.

Particularly preferably, a confocal detector is used for determining the geometrical data of the optical element. A confocal detector operates according to the principle of confocal detection, which is known from the microscopy of partially transparent tissue. In accordance with this principle, a focal point of a laser is scanned across the tissue and the light scattered back from this focal point is detected by a detector with an aperture disposed in a plane optically conjugate to the focal point. In this manner, light scattered back is differentiated from light from the surroundings, and a high imaging factor is achieved. In a normal light microscope, the image is a superposition of a sharp image of the points in the focal plane and an unsharp image of the points outside the focal plane, whereas in a confocal microscope, the excitation light is focused into the sample. Light from this focus is imaged through the same objective lens onto a pinhole, from which it is directed onto a detector (usually a photomultiplier or an APD).

Therefore, the excitation focus and the detection focus are confocal to each other, i.e., coincide.

It is also preferred to use a detector based on optical coherence tomography. This method is abbreviated as OCT and is an investigative technique in which short-coherent light is used with the help of an interferometer for measuring the distance of reflective materials. The equivalent acoustic method is ultrasound diagnostics (sonography). Thus, a three-dimensional image of the optical element can be reconstructed from reflections at interfaces of materials having different indices of refraction. This reconstruction is referred to as tomography. In the related art, this examination is used, for example, to examine the fundus or rear portion of the eye, because competing technologies, such as the confocal microscope, produce inadequate images due to a retina layer structure of about 250 to 200 μm retina and because of the small pupil size and the large distance between the cornea and the retina. In an embodiment of the present invention, unlike the practice heretofore, this method is usable in conjunction with the proposed navigation device to examine and process the eye lens.

In a preferred exemplary embodiment of the present invention, the aperture of the detection device is smaller than 0.25 and larger than 0.1, in particular smaller than 0.22 and larger than 0.18.

Using a detection device having an aperture of such a size, it is particularly preferably possible to examine the lens of an aged human eye. Especially preferably, the aperture is about 0.2.

In a preferred exemplary embodiment of the present invention, the detection device includes a polarization optical sensor system.

When using polarized light, a polarization optical sensor system makes it possible to examine the distribution of mechanical stresses in transparent bodies. When using monochromatic light, a system of dark and light stripes is produced whose arrangement allows reliable conclusions to be drawn about the distribution and magnitude of the mechanical stresses at all points of the optical body. Thus, the detection device allows the inner structures to be additionally examined with respect to the stress distribution in the optical element.

In a preferred exemplary embodiment of the present invention, the processing device includes a laser, in particular an fs laser, especially a laser producing a scanned, focused, ultra-short pulsed laser beam.

The lasers which are preferably used are scanned, focused, fs laser beams with a pulse width of less than 1 ps, particularly preferably of about 300 fs, with a pulse energy of 0.1 to 10 μJ, preferably 1 μJ, and a focus diameter of about 5 μm. The wavelength of the laser system is preferably between 400 and 1300 nm, particularly preferably between 780 and 1060 nm. The fs laser is a laser emitting high-intensity light pulses with durations in the femtosecond range. In fs lasers, energy is compressed into an extremely short time interval by mode locking. Therefore, fs lasers have significantly higher peak powers than continuous lasers. The advantages of using fs lasers include, in particular, high peak intensities, low heat transfer to the substrate, and the large spectral bandwidth. In metrology, the fs laser can also be used in the field of optical coherence tomography. Therefore, an fs laser can particularly preferably be used by the detection device to perform optical coherence tomography, and the same fs laser can be used as an element of the processing device to perform modifications and processing operations in the optical element. In that case, the detection device and the processing device largely coincide in terms of construction, because they use the same fs laser.

In a preferred exemplary embodiment of the present invention, the processing device is designed to produce radiation in the optical element in order to stimulate subdisruptively with pulse energies below or equal to 1 microJ and/or to perforate disruptively with pulse energies above 0.1 microJ and/or to cut by creating rows of narrowly spaced, disruptively produced bubbles. Thus, the processing device can be used to modify and/or process the optical element in various ways. Thus, all gradations are possible, ranging from light stimulation to the application of continuous cuts.

Due to the focused beams, ultra-short pulsed laser radiation produces a subdisruptive or disruptive modification in the target region of the beam in the optical element. A disruption is a mechanical deformation which is achieved mechanically by vaporizing material in the target region and by the resulting expansion. In the case of subdisruptive stimulation of the target region, the pulse energies used are of low intensity, so that the aforementioned mechanical effect, which is also found, for example, in ultrasound, will not occur.

Selecting pulses of higher energies will result in disruptive mechanical modification of the target region by corresponding formation of bubbles within the tissue. The individual bubbles preferably have spot diameters in the range of a few μm. Thus, it is possible to perforate the target region; i.e., to create permanent holes therein. In the case of the eye, these holes are then quickly filled with liquid or neighboring, more liquid tissue. Ultimately, this pattern and modification applied to the optical element increases the deformability of the optical element, because the removal of the corresponding material at the bombarded sites makes the overall optical element more flexible, allowing it to deform more easily. Particularly preferably, it is also possible to create rows of individual, disruptively produced bubbles having spot diameters and spot distances in the range of a few µm, and to completely superimpose said bubbles in this manner such that a continuous cut will be produced. These cutting geometries and patterns can then be applied to the eye or optical element, it being particularly preferred for said cutting geometries and patterns to extend along the detected, inner geometric structure of the optical element. With these bubble fields, an ultra-short pulsed laser system is capable of creating patterns which produce, for example, cuts extending along one of the detected interfaces at a perpendicular distance of 0.2 mm therefrom, respectively. It is also conceivable to produce cuts relative to this detected interface within the optical element at distances between 0.1 to 1 mm using sinusoidal modulation. Furthermore, these patterns are understood to be any geometric cutting patterns or bubble fields which, within the lens of the optical element, are brought into a fixed geometric relationship with an anatomical structure which has previously been detected by the measurement system.

In a preferred exemplary embodiment of the present invention, optical element (50) includes a lens, in particular an aged eye lens.

The aged eye lens frequently has hardenings which result in a loss of the accommodative ability of the eye.

Due to the phases of growth, the eye has various nuclei which differ in age and are superimposed on each other in an onion-like manner. The innermost and thus oldest nucleus hardens as it ages. By using embodiments of the present invention, it is now possible to provide an apparatus which detects the respective interface structures between the various nucleus layers and components in order to subsequently improve the flexibility of the hardened older, inner nucleus by applying suitable cutting or bubble patterns. It is also conceivable that one or more of these inner hardened nuclei could be completely removed and replaced with gel.

In a preferred exemplary embodiment of the present invention, navigation apparatus (1) includes an ophthalmologic suction/irrigation device (30) having at least one cannula (35).

Such a device is particularly preferably used to fragment and remove a hardened inner nucleus of the human eye lens and to replace it with a suitable gel. This makes it possible to replace only the innermost nucleus of the lens while the outermost layers of the nucleus of the lens are retained as a supporting structure which ensures, inter alia, that the gel introduced will remain at the location formerly occupied by the inner nucleus. Thus, the flexibility of the eye lens, and thus its accommodative ability, can be significantly improved.

This is particularly preferably done using an ophthalmologic suction/irrigation device, such as is used in phacoemulsification. Such a suction/irrigation device typically includes one or two cannulas through which the fragmented nucleus can be removed. Thus, an fs laser can be used to reduce the inner nucleus of an eye lens to small fragments having a diameter of less than 1 mm, which can be suctioned off through a suction/irrigation device. This prepared lens nucleus is completely removed using a suction/irrigation device such as is used, for example, in the conventional phacoemulsification technique, or by way of a device using a different suction/irrigation principle. The resulting hollow lens body can now preferably be filled with an artificial or natural, biocompatible, flexible, transparent gel material through a cannula, or preferably bimanually; i.e., using two cannulas inserted at opposite sides, so as to restore the optical function and accommodative ability of the lens.

Particularly preferably, the cannula has a tip which is configured such that when it is inserted, in particular into the lens cortex, it will urge the material sideways and not forward, so that a self-sealing effect will be produced after the gel filling process is complete. This short-pulsed laser assisted, partial phacoemulsification prevents the development of a secondary cataract and, in addition, avoids a shortcoming of the currently clinically studied gel fillings of the which are introduced into the capsular bag after a preceding complete phacoemulsification. The problem here is that the entire nucleus of the lens must be removed, as a result of which the gel cannot be adequately fixed in place. In addition, remaining proliferating cells of the removed lens may produce an opacity of the posterior membrane of the capsular bag. This secondary cataract (posterior opacity) is conventionally treated by photodisruption using a Q-switched Nd:YAG laser, whereby the opacified posterior membrane of the capsular bag is removed from the optical path of the eye. However, if the capsular bag is completely filled with gel, this method cannot be used because the gel would flow out. By the partial gel filling within the cortex of the natural lens in accordance with an embodiment of the present invention, on the one hand, the secondary cataract rate is significantly reduced and, on the other hand, the gel is additionally encapsulated and, in particular, the hard nucleus is replaced by a flexible gel so as to restore the accommodative ability.

In another preferred embodiment, after the lens body produced by the partial phacoemulsification has been filled, the filling material introduced is exposed to electromagnetic radiation, for example UV radiation, which produces a change in the consistency and/or viscosity of the gel. In this manner, the gel is prevented from leaking or escaping from the lens body at a later time.

In another advantageous embodiment, the treatment with electromagnetic radiation, for example UV radiation, may be used to subsequently fine-tune the refractive power of the new gel-like lens nucleus by way of objective and/or subject assessment by the patient.

The inventive apparatus for navigated intraocular, ultra-short pulsed laser cutting can also be used for ultra-short pulsed laser fragmentation of the entire lens in the conventional phacoemulsification of the entire lens. There is then no need to conventionally liquefy the lens using ultrasonic vibrations. Instead, the lens fragments produced by the above-described laser cuts can simply be suctioned off using the suction/irrigation device. This novel method reduces the duration of the invasive surgery and the thermal load on the eye.

Furthermore, the inventive apparatus for navigated intraocular, ultra-short pulsed laser cutting can be used for cutting of the posterior membrane of the capsular bag in order to treat secondary cataracts. Unlike the conventional ns Nd:YAG-Laser, the fs laser provides for a gentler treatment because of the lower disruptive energies, which are reduced from several mJ to a few µJ. When using conventional Nd:YAG disruptive lasers, the focus is located behind the membrane of the capsular bag in order to destroy the membrane by way of the acoustic shock wave and to safeguard the artificial lens, whereas when using the high repetition fs laser and the coupled navigation, the focus will be located on or in the immediate vicinity of the membrane.

An embodiment of the present invention provides an apparatus for planning the therapy of a human eye, the apparatus comprising a dynamic wavefront measurement device (aberrometer) for acquiring wavefront data, and a diagnostic device for determining geometric parameters of the optical apparatus of the eye (an anterior chamber OCT and/or a rotating Scheimpflug camera and/or an ultrasonic 3D measurement system and/or eye length measurement devices and/or a topography measurement device), and further comprising a controller for consistent superposition of the acquired wavefront data and geometric data, and an additional controller for planning the most efficient therapeutic laser cutting paths.

The dynamic wavefront measurement device used may be an aberrometer. Such a device is used to acquire wavefront data of the entire eye.

The diagnostic device used for determining geometric parameters of the optical apparatus of the eye may be an anterior chamber OCT and/or a rotating Scheimpflug camera and/or an ultrasonic 3D measurement system and/or eye length measurement devices and/or a topography measurement device. Such a device is used, in particular, to acquire data of the lens.

A first software package is used in conjunction with the controller to achieve a consistent superposition of the acquired wavefront data and geometric data. This produces an overall image of the lens and of the overall optical apparatus of the eye.

A second software package is used in conjunction with an additional controller to plan the most efficient therapeutic laser cutting paths. This is preferably done using the same controller as in the previous step. In this connection, it is possible to take into account not only the geometry of the lens, but also any visual defects of the overall apparatus, thus making it possible to determine a cutting path which takes into account the individual conditions of this eye and which will improve the accommodative ability thereof. This determination can be done using, for example, the finite element method.

An embodiment of the present invention provides a method for modifying an optical element, in particular a human eye lens, using a preferably scanned, focused and pulsed laser beam, the modification being performed in accordance with the following steps: completely measuring the dynamic optical wavefront of the eye during accommodation and the associated geometric parameters to individually plan an fs-laser cutting therapy; detecting the position, geometry and inner structure of the eye lens; selecting a basic cutting pattern composed of a plurality of planes; developing a protocol defining the cutting paths by adapting or converting the basic pattern to match the detected individual geometry of the eye lens; indifferentiating the positioning system with respect to the position of the eye lens; and making the surgical cuts using the laser system according to the established protocol.

FIG. 1 shows, in a schematic view, a navigation apparatus 1 according to an embodiment of the present invention. Navigation apparatus 1 includes a detection device 10, which is equipped with an optical confocal and/or optical coherence tomography device and with a polarization optical sensor system 15. Also provided is a processing device 20. Detection device 10 and processing device 20 are connected to a controller 40. A suitable optical path may extend from detection device 10 and processing device 20 via scanning mirrors into an optical element 50, here a multilayered lens. In lens 50, various inner structures of the optical element are denoted by reference numeral 55.

The inner structure 55 of lens 50 is detected by detection device 10. This process is assisted by a sensor system 15, which makes it possible to obtain a three-dimensional image of this inner structure 55 that is even more comprehensive and is also dependent on the stress ratio. Preferably, detection device 10 also includes a device for dynamic wavefront diagnosis to measure the range of accommodation of the optical element or eye lens during positive accommodation and negative accommodation, and to measure the speed at which the range of accommodation is traversed. Preferably, detection device 10 also detects visual defects, the topography of the cornea and the respective pupil size, as well as illumination parameters of the stimulation target. It is particularly preferred to selectively dynamically analyze the sphere, the cylinder, or any higher-order aberrations. In addition, detection device 10 can also acquire geometric data of the eye, using, for example, devices based on optical coherence tomography or rotating slit Scheimpflug cameras, confocal laser scanners, and by ultrasonographs. This information is transferred to controller 40 which calculates target coordinates for processing device 20 using a finite element model. Particularly preferably, the data is first transferred to the controller in order for it to calculate preferred cutting geometries which, when applied to the eye, will, for example, increase the accommodative ability. Thus, a pattern that is likely to provide the highest increase in the amplitude of accommodation can be determined using, for example, the finite element method. Thus, when the simulation is completed, shot parameters are provided which will then by used by the laser to apply these cutting geometries to the optical element and/or eye lens. The controller passes this data on to processing device 20, from where the lens 50 will be processed in the predetermined manner. The shot pattern and the cutting geometries being applied are oriented relative to inner structure 55 of lens 50. This makes it possible to make therapeutic cuts which extend along the detected planes, or along geometric structures associated with these planes, and which are produced, for example, by way of bubble fields produced by a processing device 20 in the form of an ultra-short pulsed laser system. Thus, an embodiment of the present invention provides the advantage of a diagnostically and therapeutically coupled system for carrying out suitable and minimally invasive therapies in a manner that is adapted in the best possible way to the individual anatomy of a human eye lens. Natural slip planes are regenerated by way of the anatomically coupled cutting paths, which ensures high physiological compatibility of the therapy.

FIG. 2 shows, in a schematic view, the construction of the human eye. Also shown are cutting patterns, which have been applied using the inventive apparatus shown in FIG. 1.

As an optical element 50, the structure of a human eye is designated by reference numeral 50. The eye has an individual geometry and anatomically existing discontinuity planes, such as interfaces between the various components of the nucleus. The figure shows embryonic nucleus 55a, fetal nucleus 55b, adult nucleus 55c, and cortex 55d. The anterior capsule is denoted 55e. Thus, eye 50 contains natural interfaces or boundaries, for example, between embryonic nucleus 55a and fetal nucleus 55b and between fetal nucleus 55b and adult nucleus 55c, etc. These interfaces are represented in the figure by continuous lines. Also plotted are dotted or dashed lines representing cutting patterns 25. Thus, for example, a cutting pattern 25' extends on the side of fetal nucleus 55b along the interface between fetal nucleus 55b and adult nucleus 55c. This cutting pattern 25' extends in a sinusoidal pattern along the interface or inner structure 55 of lens 50. Also shown are cutting patterns 25a and 25a', which have been created near the interface between adult nucleus 55c and fetal nucleus 55b on the side of the adult nucleus in approximately parallel relationship with said interface and at a predetermined distance therefrom.

By the application of the cutting patterns 25, which extend along the detected planes, or along geometric structures associated with these planes, and which are produced by way of bubble fields produced by an ultra-short pulsed laser system, these act as anatomically coupled cutting paths and increase the flexibility of the interface between fetal nucleus 55b and adult nucleus 55c. In this manner, the eye can accommodate better and partially loses the limitations caused by age-related hardening of the lens nucleus. Particularly preferably, the cutting path used for applying cutting pattern 25 starts at the point within the eye that has the greatest distance from the apex of the cornea in order to ensure the best possible focus quality of the laser spot and to successively produce scattering centers for the parasitic laser radiation of the following laser spots. In this manner, the retinal laser load can be minimized.

FIG. 3 shows, in a schematic view, two cutting patterns in the optical element. The figure consists of two subfigures, namely FIG. 3a and FIG. 3b, showing different cutting patterns, respectively.

FIG. 3a is a very schematic, simplified view of a lens 50 having an inner structure 55 in the form of a hardened inner nucleus. The dashed lines represent a first possible cutting pattern geometry 25, which is intended to increase the flexibility and, thus, the accommodative ability of lens 50. The cuts forming cutting pattern 25 extend radially outward from the center of the lens nucleus and end at geometric discontinuity planes 55 of the lens. Due to the cylindrical geometry of the lens, the cuts shown in a cross-sectional view are made on cone segments. In FIG. 3a, the cuts extend only in the nucleus of the lens, because this is where the rigidity of the lens is greatest and, consequently, where a maximum effect can be achieved to restore the accommodative ability.

FIG. 3b shows a pattern 25, which is particularly beneficial for patients who are expected to develop a cataract in the nucleus. The radial cuts are only made in the cortex. In addition to the radial cuts, a further cut is made along the discontinuity plane between the nucleus and the cortex. The cutting pattern is preferably produced in a known manner using a scanned, focused, fs laser beam with a pulse width of less than 1 ps (preferably 300 fs), with a pulse energy of 0.1 to 10 µJ, preferably 1 µJ, and a focus diameter of about 5 µm. The wavelength of the laser system is preferably in the range between 400 and 1300 nm, particularly preferably between 780 and 1060 nm.

Preferably, the anatomically coupled cutting paths do not extend across the entire lens diameter, but only in a peripheral area, an optical zone of the eye having a diameter of, for example, 3 mm, preferably 2 to 7 mm, being left untreated, or being treated only in a central pupil area having a diameter of, for example, 7 mm. In that case, a peripheral area remains untreated. When the treatment is performed in the peripheral area, it is preferred to use mirror contact glasses, whereas when the central area is treated, simple contact glasses are used.

FIG. 4 shows, in a schematic view, a further embodiment of the present invention, which is used in partial phacoemulsification. Similarly to FIG. 2, FIG. 4 shows a schematic cross-section through the human eye, illustrating the various nuclei and corresponding interfaces. FIG. 4 shows that embryonic nucleus 55a and fetal nucleus 55b (here crisscross hatched) were emulsified; i.e., the nuclei were reduced to fragments having a diameter of less than 1 millimeter. Also shown is a cannula 35, which is laterally inserted into lens 50 and through which the fragmented material can then be removed. After that, a suitable gel filling can then be introduced therethrough. It should be noted that it is particularly preferred to use two cannulas 35, the second cannula being inserted into the lens from the other side, which is not depicted because only half of the lens is shown here. In this way, it is possible to suction material off through one cannula while introducing irrigation fluid through the other cannula so as to assist or improve the removal process. Subsequently, the gel can be introduced in the same manner, and the remaining irrigation fluid, which is displaced by the gel, can be removed through the aspiration cannula. Ideally, material is continuously supplied through one cannula while the other cannula is used to continuously suction off material therethrough.

In this manner, the inner hard nucleus of the aged human eye lens is cut out by the scanned, short-pulsed laser spots, and is at the same time reduced to small fragments with a diameter of less than 1 mm, which can be suctioned off by a suction/irrigation device. In this case, the inner hard nucleus includes the two segments embryonic nucleus 55a and fetal nucleus 55b, but it could also include only one nucleus.

This prepared nucleus of the lens is then completely removed using a suction/irrigation device such as is used in the conventional phacoemulsification technique, or by way of a device using a different suction/irrigation principle. In accordance with an embodiment of the present invention, the resulting hollow lens body is now filled with an artificial or natural, biocompatible, flexible, transparent gel material through a cannula, or preferably bimanually; i.e., using two cannulas inserted at opposite sides, so as to restore the optical function and accommodative ability of the lens. These cannulas, which have a diameter of about 1 mm, are preferably used to penetrate the eye, including the capsular bag and the lens cortex. The punctures are preferably made angularly during the preparation, so as to make it possible to take advantage of the self-sealing effect after the treatment. In addition, it is particularly preferred to select the consistency of the gel depending on the diameter of the punctures in such a way that the openings will close. Particularly preferably, the tips of the cannulas are designed such that when they are inserted, in particular into the lens cortex, they will urge the material sideways and not forward, so that a self-sealing effect will be produced.

This preferably short-pulsed laser assisted, partial phacoemulsification prevents the development of a secondary cataract and, in addition, avoids a shortcoming of the currently clinically studied gel fillings of the which are introduced into the capsular bag after a preceding complete phacoemulsification. This shortcoming is that the secondary cataract, which occurs in 50 percent of cases as a result of remaining proliferating cells of the removed lens, which produce an opacity on the posterior membrane of the capsular bag, is treated conventionally by photodisruption using a Q-switched Nd:YAG laser. In this treatment, the opacified posterior membrane of the capsular bag is completely removed from the optical path of the eye. It is then no longer possible to completely fill the capsular bag with gel, because the gel would flow out. By the partial gel filling within the cortex of the natural lens according to an embodiment of the present invention, on the one hand, the secondary cataract rate is significantly reduced and, on the other hand, the gel is additionally encapsulated.

In partial phacoemulsification, which is used to partially remove the lens in the form of an inner nucleus, cutting is performed along a complete path along the inner nucleus. In addition, the nucleus to be removed is reduced to fragments using efficient geometric cutting patterns. Particularly preferably, the procedure starts at the point within the eye that has the greatest distance from the apex of the cornea in order to ensure the best possible focus quality of the laser spot and to successively produce scattering centers for the parasitic laser radiation of the following laser spots, and to thereby reduce the retinal laser load.

Particularly preferably, after the filling of the lens body produced by the partial phacoemulsification, the filling material introduced is exposed to electromagnetic radiation, for example UV radiation, which produces a change in the consistency and/or viscosity of the gel. This makes it possible, firstly, to prevent the gel from leaking or escaping from the lens body at a later time. Secondly, the refractive power of the new gel-like lens nucleus can subsequently be fine-tuned by way of objective and/or subject assessment by the patient. This makes it possible to produce a refractive index gradient in the regenerated lens, which will be efficient for the dynamic refraction.

Thus, a human eye is initially examined to fully determine the wavefront dynamics (does the eye still have an accommodation range of 4, 3, 2 or 1 diopters). Moreover, it is preferred to determine the associated, individual geometric shape for the minimum respective positive and negative accommodation (curvature of the anterior and posterior sides of the lens and distances of the optical planes). From this data, a complete description of this individual optical/geometrical system is generated by a software, for example, based on the finite element method. An additional software can be used to calculate therefrom the optimized cuts to be made in the lens by way of the laser system.

Thus, an ophthalmo-surgical device system is provided, and instructions for using it, for preparing or removing transparent biological tissue in a gentle and accurate manner, especially in the eye, and more particularly in the human eye lens, during refractive laser surgery or cataract surgery, especially to treat presbyopia by restoring the accommodative ability of the lens body.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS

1 Navigation apparatus
10 detection device
15 polarization optical sensor system
20 processing device
25 cutting pattern
30 ophthalmologic suction/irrigation device
35 cannula
40 controller
50 optical element/lens
55 inner structure of the optical element/lens

What is claimed is:

1. A method for modifying an optical element using a laser beam, the method comprising:
    measuring a dynamic optical wavefront produced by the optical element during accommodation;
    measuring geometric parameters associated with the dynamic optical wavefront;
    planning a fs-laser cutting therapy based upon the measured geometric parameters;
    detecting a position, a geometry, and a structure of the optical element;
    determining a basic pattern of the detected geometry of the optical element;
    selecting a basic cutting pattern composed of a plurality of planes;
    developing a protocol defining a cutting path based on the basic pattern of the detected geometry; and
    modifying the optical element using the laser beam according to the protocol.

2. The method as recited in claim 1, wherein the optical element is a human eye lens.

3. The method as recited in claim 1, wherein the modifying is performed by surgical cuts.

4. The method as recited in claim 1, further comprising fragmenting and removing an inner nucleus of the optical element.

5. The method as recited in claim 4, further comprising filling the inner nucleus with a gel.

* * * * *